US006383750B1

(12) United States Patent
Guillet et al.

(10) Patent No.: US 6,383,750 B1
(45) Date of Patent: May 7, 2002

(54) LABELLING OF POLYMERS AND SEQUENCING OF NUCLEIC ACIDS

(75) Inventors: James E. Guillet; Nicholas A. Burke, both of Ontario (CA)

(73) Assignee: Premaxis Technology Ventures, Inc., Toronto (CA)

(*) Notice: Subject to any disclaimer, the term of this patent is extended or adjusted under 35 U.S.C. 154(b) by 0 days.

(21) Appl. No.: 09/530,043

(22) PCT Filed: Oct. 22, 1998

(86) PCT No.: PCT/CA98/00981

§ 371 Date: Nov. 27, 2000

§ 102(e) Date: Nov. 27, 2000

(87) PCT Pub. No.: WO99/22020

PCT Pub. Date: May 6, 1999

Related U.S. Application Data

(60) Provisional application No. 60/064,838, filed on Oct. 23, 1997.

(51) Int. Cl.[7] ............................ C12Q 1/68; C07H 19/00; C07H 21/00
(52) U.S. Cl. ...................... 435/6; 435/91.1; 435/91.2; 536/22.1; 536/23.1
(58) Field of Search .................. 435/6, 91.1, 91.2; 536/22.1, 23.1

(56) References Cited

FOREIGN PATENT DOCUMENTS

| EP | 0131830 A1 | * | 1/1985 |
| WO | 91 13080 A | | 9/1991 |
| WO | WO 97/05156 | * | 2/1997 |

OTHER PUBLICATIONS

Holdcroft et al. "Two–Photon Chemistry. 1. Fluorescence labeling of polystryene and poly(methyl methacrylate) by laser photolysis of 2–naphthylmethyl 1–naphthylacetate" Macromolecules, pp. 1210–1212, 1991.*

Tang et al. "A preparative Synthesis of lumiphore–labeled polymers" Macromolecules, pp. 5487–5490, 1994.*

* cited by examiner

Primary Examiner—Jezia Riley
(74) Attorney, Agent, or Firm—Nixon & Vanderhye

(57) ABSTRACT

Polymers are randomly labelled with labelling groups such as fluorophores, by a process of creating free radicals on the polymer in the presence of a stable free radical, such as an aminooxyl compound, so that the stable free radical group bonds to the polymer in random fashion. Labelling groups such as fluorophores are attached to the stable free radical groups, before or after they are attached to the polymer. The process allows labelling of polymers having no reactive functional groups, it can also be applied to the labelling of nucleic acids, for use in conjunction with a PCR chain extension sequencing process, to allow the sequencing of target nucleic acids of high molecular weight.

25 Claims, 13 Drawing Sheets

LABELLING OF POLYMERS AND SEQUENCING OF NUCLEIC ACIDS

Figure 1:
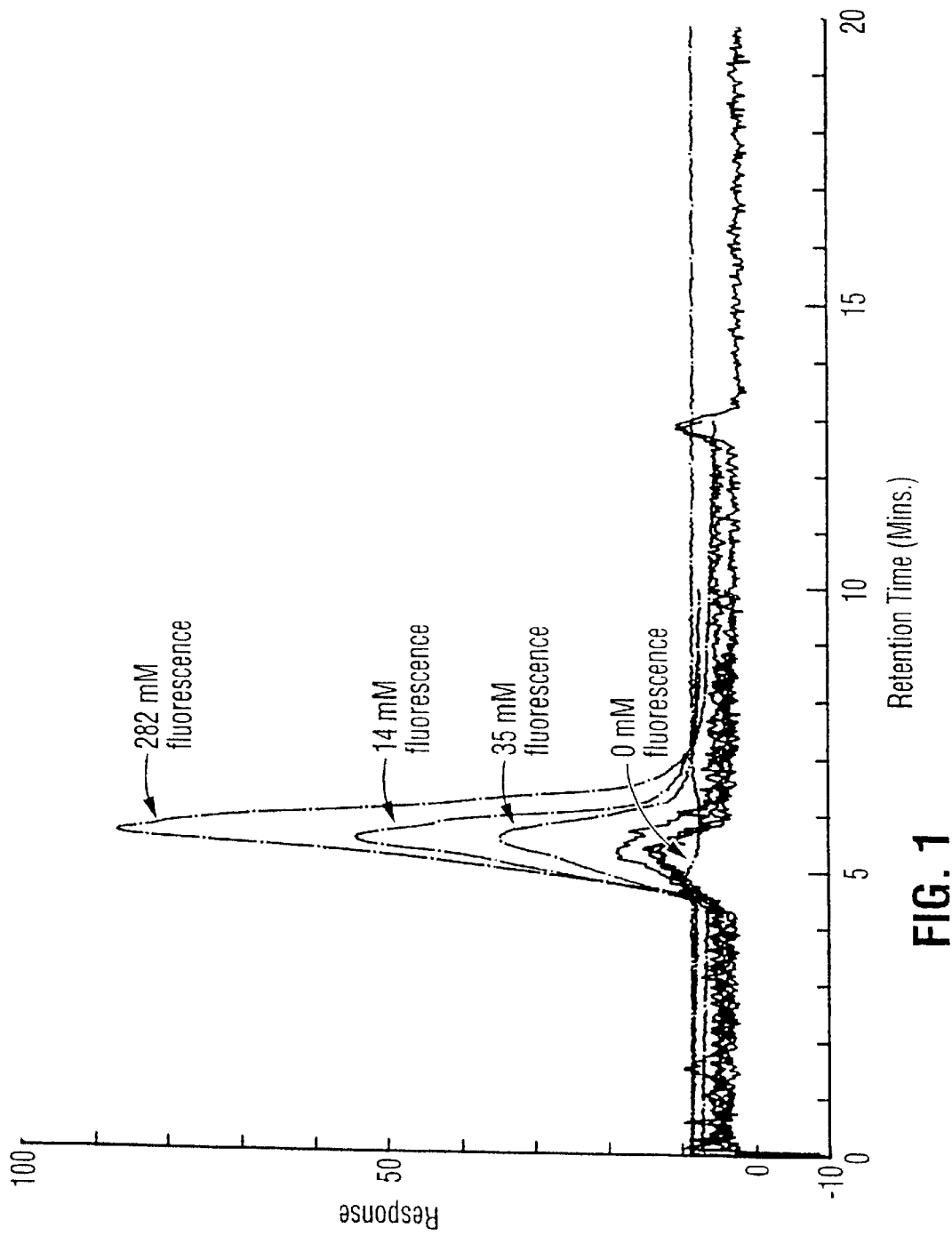

This application is a 371 of PCT/CA98/00981 filed Oct. 22, 1998 and now expired, which claims benefit of U.S. Provisional application No. 60/064,838 filed Oct. 23, 1997 and now expired.

FIELD OF THE INVENTION

This invention relates to polymers having functional groups attached thereto at random positions along their polymeric chains, hereinafter referred to as "labelled polymers". It also relates to processes for preparing labelled polymers.

BACKGROUND OF THE INVENTION

The introduction of labels onto polymer chains is a subject of considerable interest. With the introduction of a small number of groups on a polymer chain, it is possible to make dramatic changes to some polymer properties while leaving others essentially unchanged. For instance, the introduction of several fluorophores per polymer chain will render the polymer easily detectable by highly sensitive fluorescence techniques while having little effect on properties such as mechanical strength, solubility, glass transition and melting temperature, etc. Similarly, the introduction of several biologically active groups per chain may turn an inert polymer into one which is biologically active, is readily bound to biomaterials (biocompatible), or one with medical applications (i.e. drug delivery, diagnostics).

There are two general means by which "labelled" polymers are prepared.

In the first method for labelling, a small amount of monomer bearing the label is polymerized with the bulk monomer(s). If the labelled monomer is incorporated in a small amount the desired polymer is obtained. Although this approach has been widely and successfully utilized, it has several drawbacks. Monomer synthesis is often required, some labels may not tolerate polymerization conditions, and the labelled polymer might not match the properties, in particular molecular weight, of an unlabelled control sample.

The second technique for "labelled" polymer synthesis is by polymer modification, in which labels are bound to an existing polymer. This is relatively straightforward for polymers with pendant functional groups such as amino, hydroxy or carboxylic acid groups. Thus, it is possible to use conventional chemistry to label polymers such as poly (acrylic acid), poly(allylamine) or poly(vinyl alcohol). In the case of biopolymers (peptides, membranes, polysaccharides, etc.), there are well developed techniques for labelling. However, it is more difficult to label polymers such as poly(ethylene), poly(propylene), poly(styrene), poly (ethylene oxide), poly(vinyl chloride), polyvinyl acetate), poly(methyl methacrylate), etc. which lack reactive functional groups. Some of these polymers such as poly(styrene) and poly(methyl methacrylate) can be labelled using more drastic conditions such as Friedel-Crafts reactions or transesterification, but many are resistant to even these more forceful approaches.

BRIEF REFERENCE TO THE PRIOR ART

B.-Z. Tang, S. Holdcroft, J. E. Guillet, *Macromolecules*, 27, 5487 (1994); and S. Holdcroft, J. E. Guillet, *Macromolecules*, 24, 1210 (1991); S. Holdcroft, B.-Z. Tang, J. E. Guillet, *Chem. Commun.*, 1991, 280 disclose processes for binding fluorophores to polymers which cannot easily be labelled by conventional means. In these processes, photochemically generated free radicals are used to abstract a hydrogen atom from the polymer, in the presence of a second, fluorophore-bearing radical generated in the same or a parallel reaction. The fluorophore-bearing radical can then react with the polymer-centered radical to produce a fluorophore labelled polymer. A problem with this approach is that radical recombination and other side reactions are likely to take place, to consume many of the fluorophore-bearing free radicals, and if the lifetime and concentration of such free radicals is low, many polymer centered radicals will not be captured by them.

It is an object of the present invention to provide a novel process for preparing labelled polymers.

It is a further object of the invention to provide novel labelled polymers.

It is a further and more specific object of the present invention to provide novel, labelled nucleic acids, a process for their preparation, and a process of determining the sequence of a target nucleic acid using such novel, labelled nucleic acids.

SUMMARY OF THE INVENTION

The present invention provides, from one aspect, a process of labelling polymers by a free-radical mechanism, in which one reagent or mechanism is used to generate a free radical on the polymer (the polymer-centered radical), and a second reagent is used to generate a trapping radical which captures the polymer-centered radical. The labelling group (e.g. a fluorophore) may be bound to the trapping radical, i.e. it may be part of the second reagent. Alternatively, it can be added in a separate reaction, to bind to the trapping radical after attachment thereof to the polymer.

The second reagent used as a trapping radical is suitably one which will generate a stable free-radical. Stable free radicals are species which will not react with themselves, and which can exist for extended periods of time, at least one second, in solution or in the solid state. They will react rapidly with the polymer-centered (C-centered) free radicals, but not with most oxygen centered radicals. As a result, it is possible to prepare solutions of stable free-radicals at relatively high concentrations, to ensure efficient capture of the polymer-centered radicals.

Thus according to this aspect of the invention, there is provided a process of labelling a polymer with functional groups randomly distributed along the polymer backbone chain, which comprises:

generating polymer-centered free radicals at random position along the chain of a polymer;

reacting the polymer-centered free radicals so formed with stable free radicals to attach stable free radical derived groups thereto at random location along the polymer chain;

and attaching functional, labelling groups to the stable free radical derived groups, before or after the reaction thereof with the polymer-centered free radicals on the polymer chain.

BRIEF REFERENCE TO THE DRAWINGS

Figure 2:
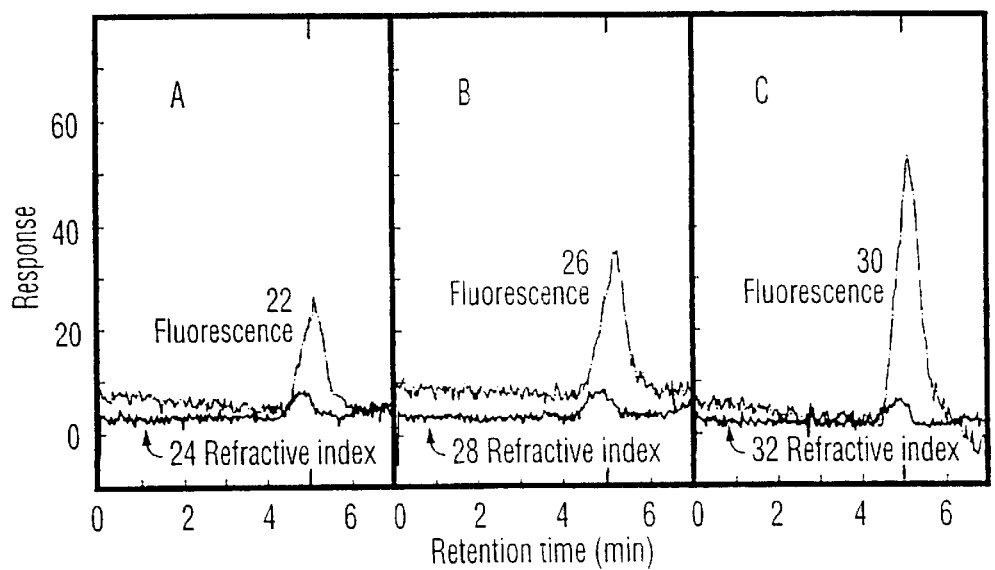
Figure 3:
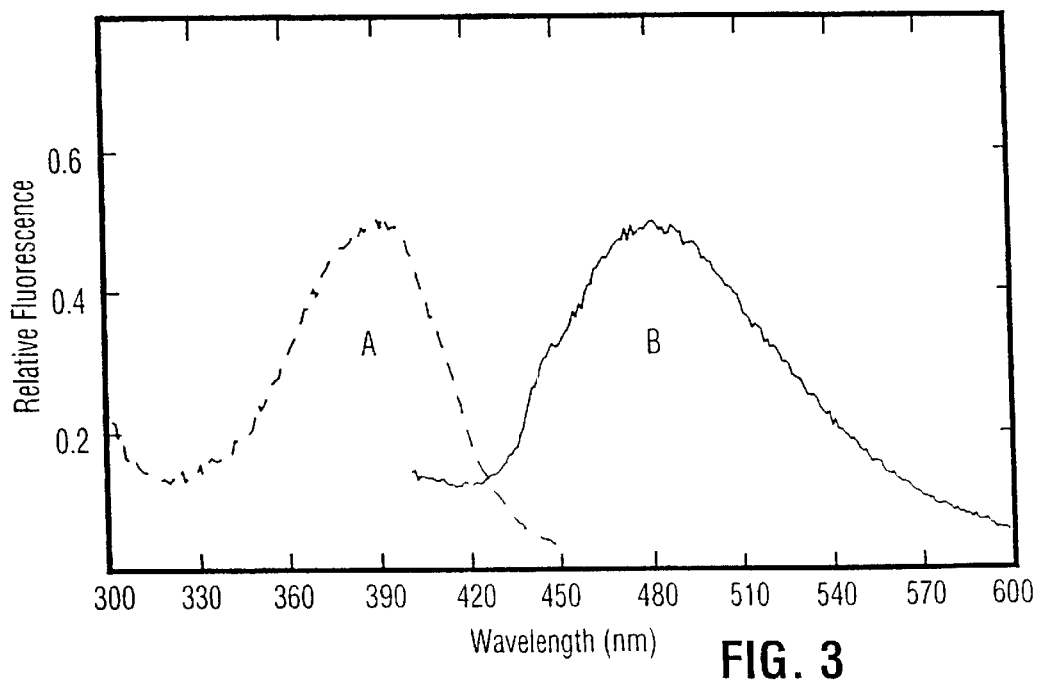
Figure 4:
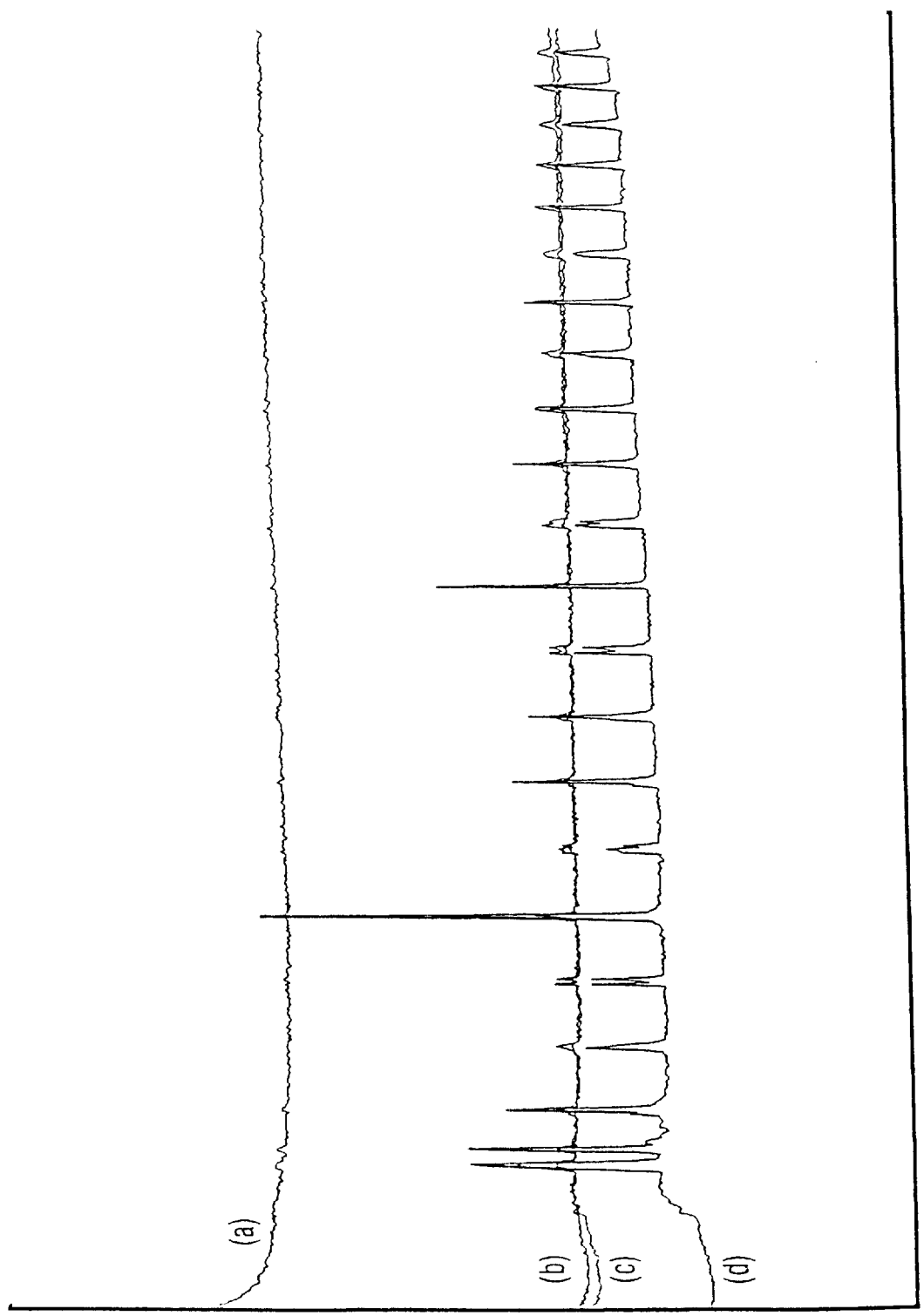
Figure 5:
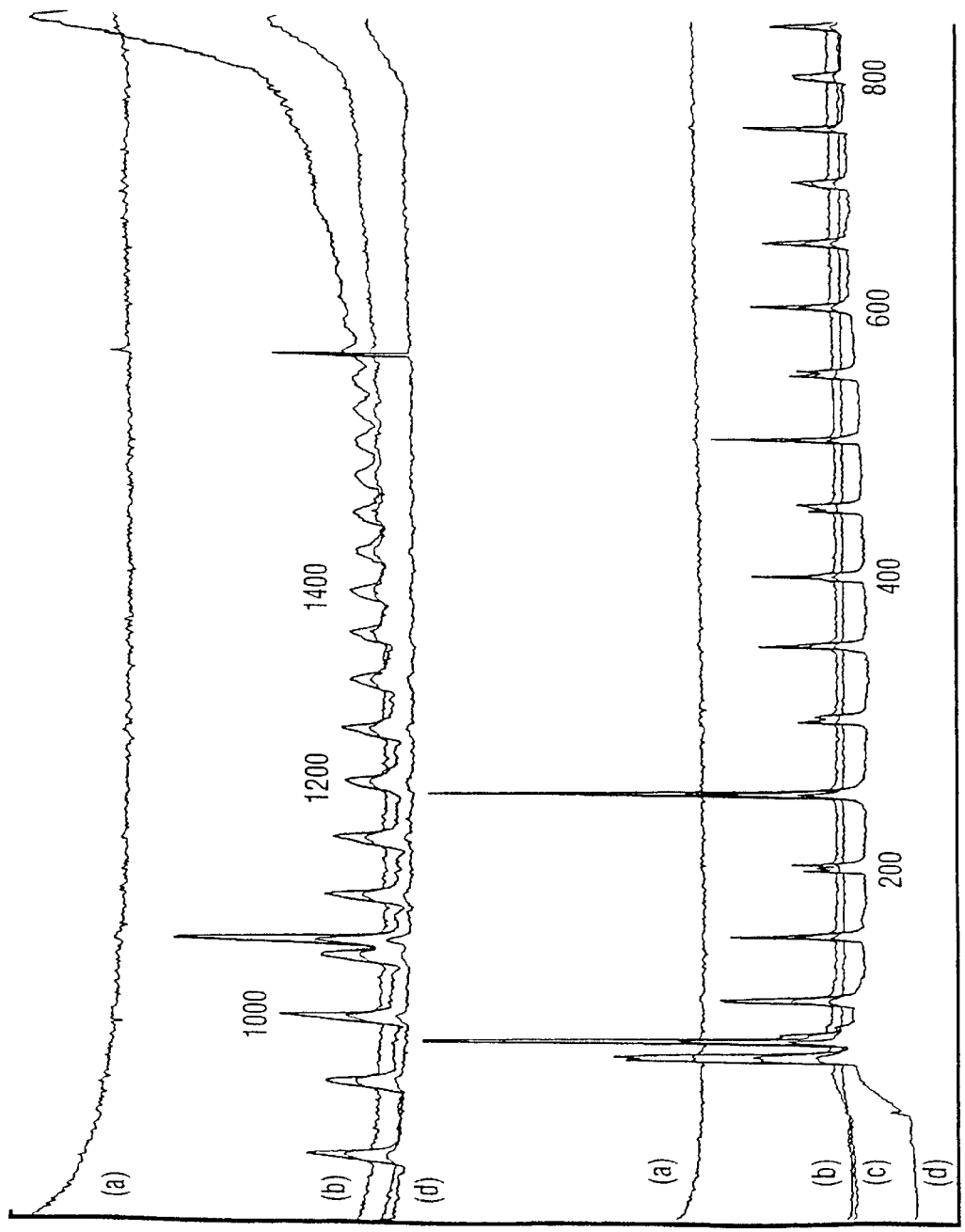
Figure 11:
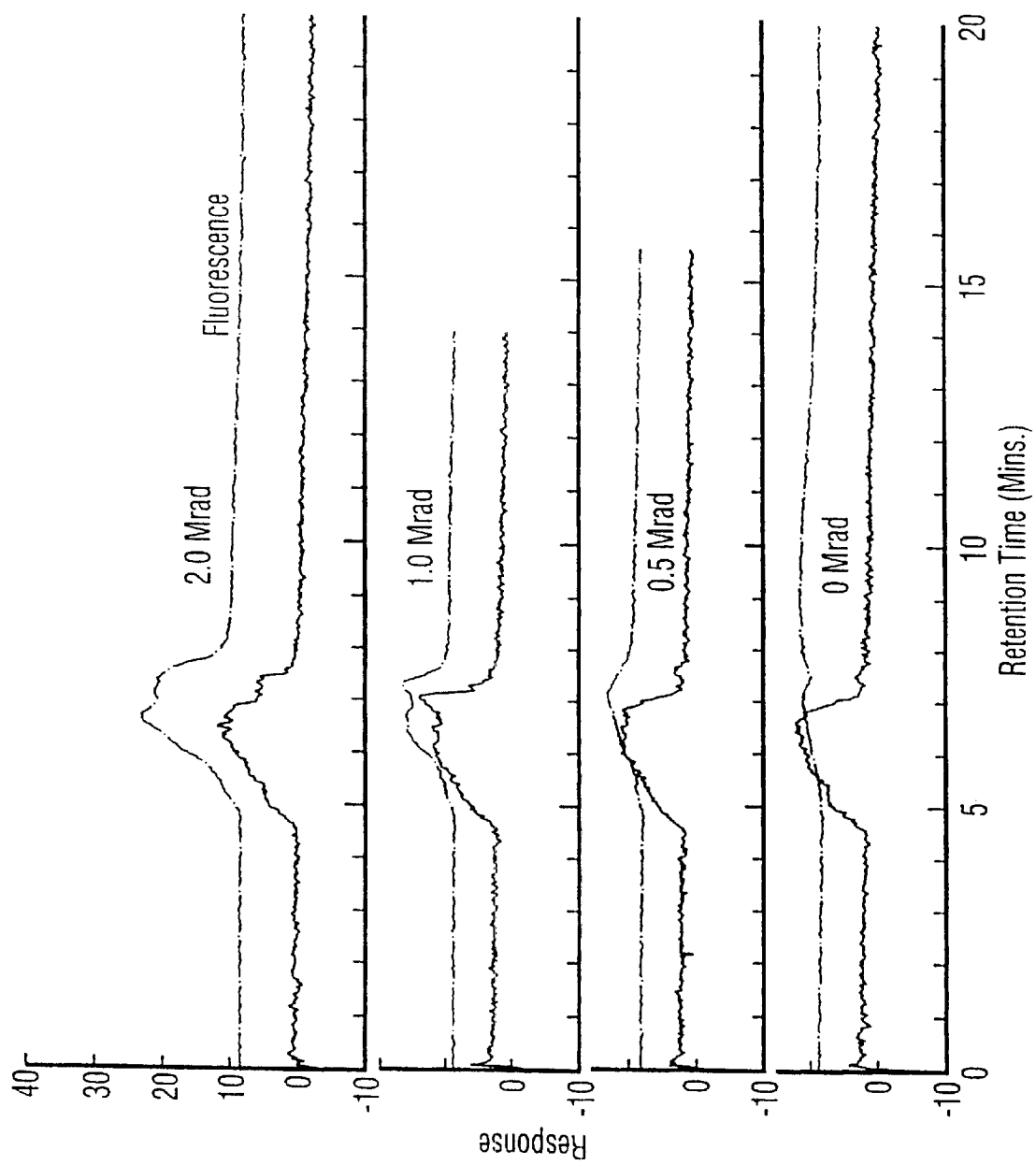
Figure 12:
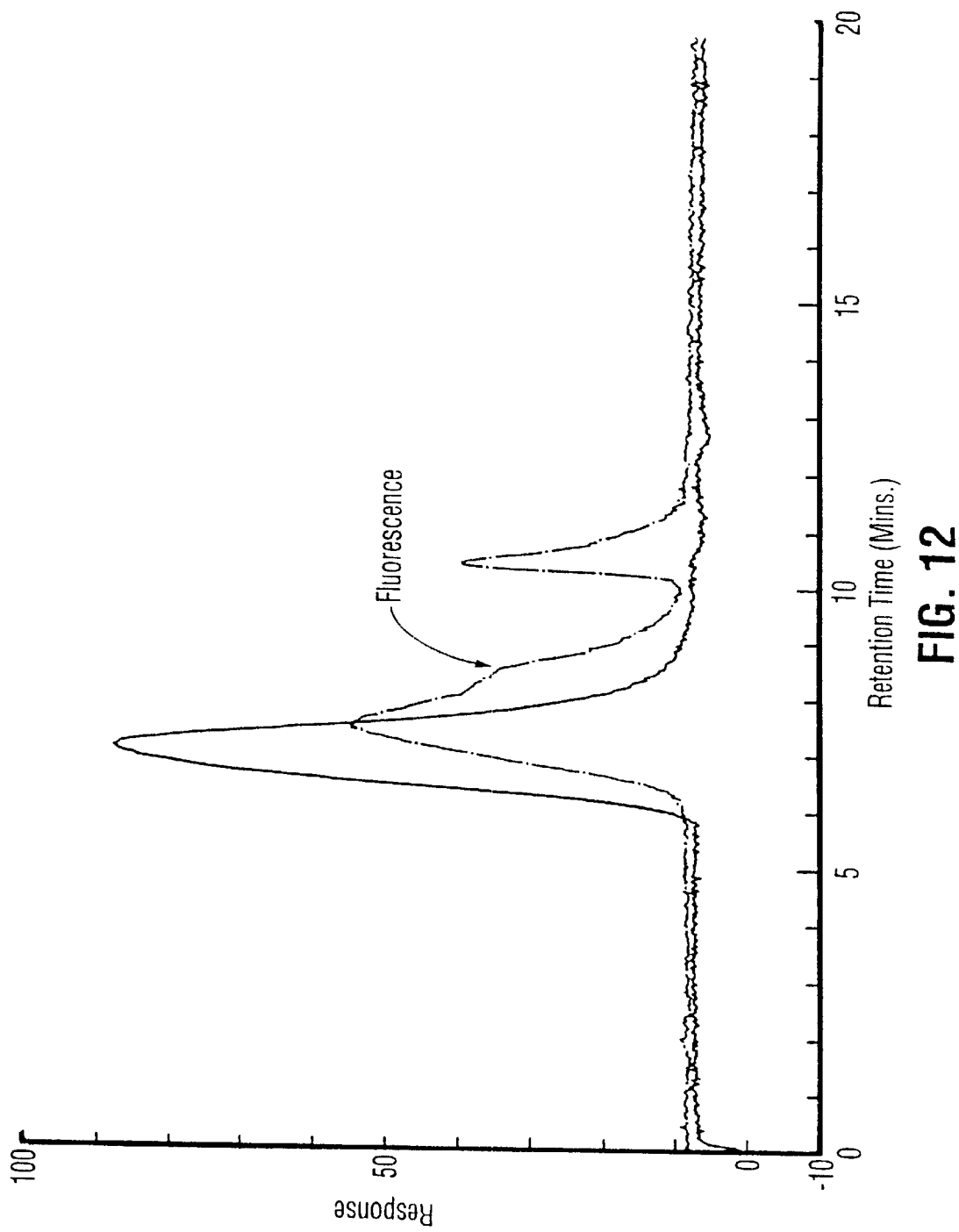
Figure 13:
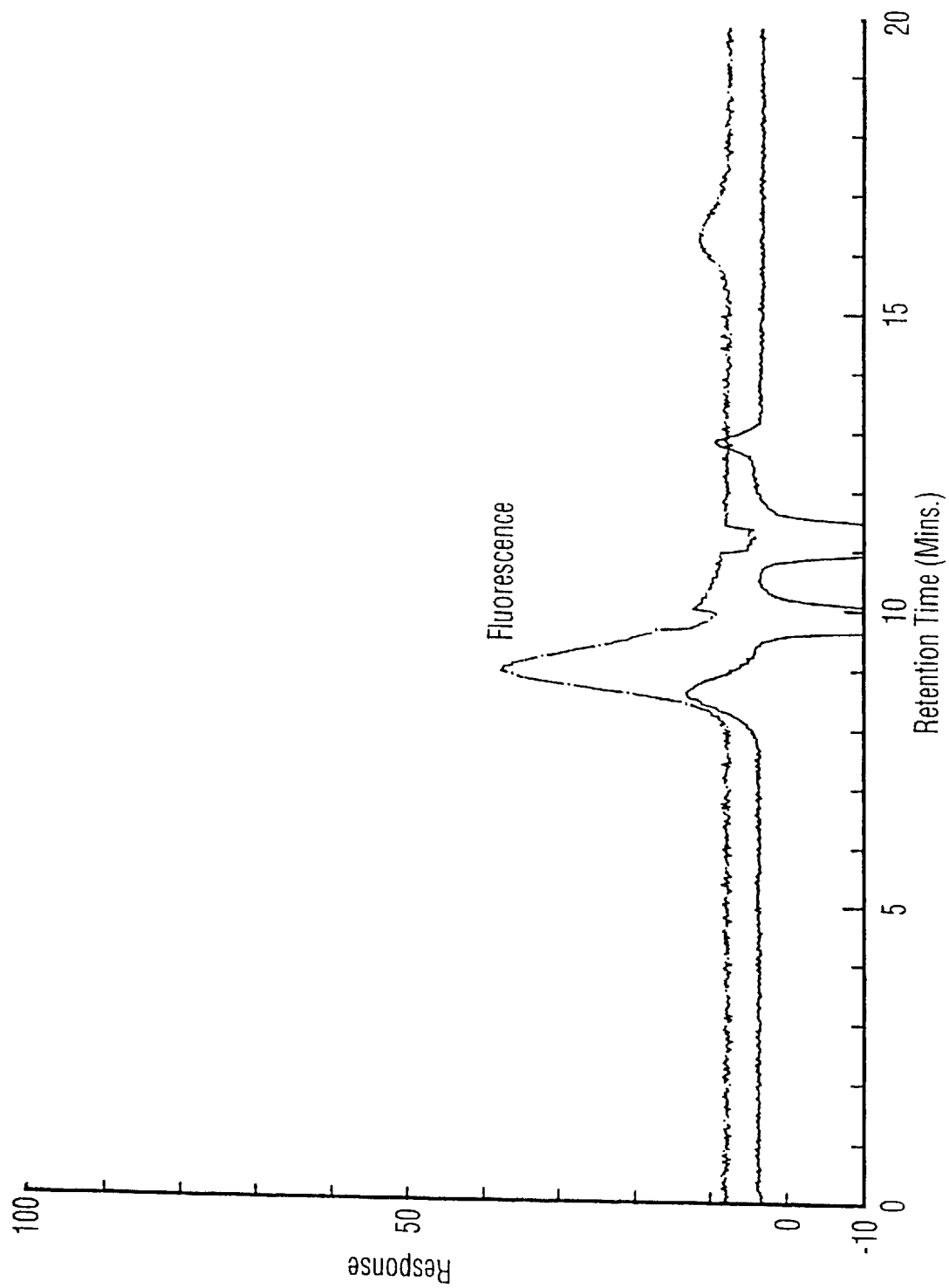
Figure 14:
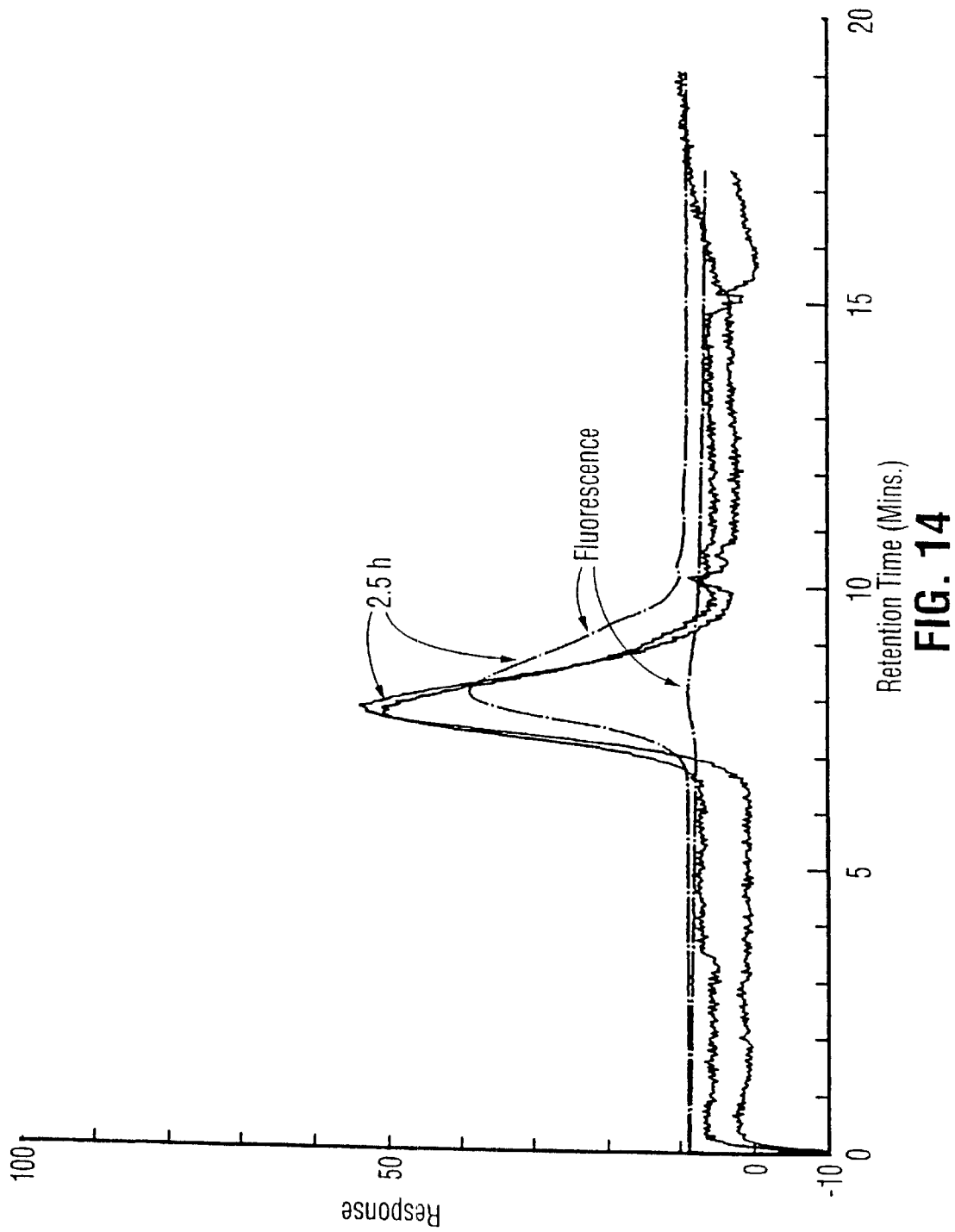

FIG. 1 presents GPC chromatograms obtained from the products of Example 1 below;

FIG. 2 presents GPC chromatograms obtained from the products of Example 2 below;

FIG. 3 is the excitation spectrum and the emission spectrum of the products of Example 2 below;

FIGS. 4 and 5 present fluorescence intensity scans, from an automatic sequencer, for the products of Example 4 below;

FIGS. 6, 7, 8, 9 and 10 present GPC traces for the products of Example 5 below;

FIGS. 11 and 12 are GPC traces of products produced according to Example 6 and described below; and FIGS. 13 and 14 are GPC traces of products produced according to Example 7 described below.

DESCRIPTION OF THE PREFERRED EMBODIMENTS

Suitable backbone polymers for labelling according to the present invention include substantially any polymer on which suitable free radical sites can be generated. The polymers include hydrocarbon polymers such as polyethylene, polypropylene, polystyrene, polybutylene, other polyolefins and the like, and unsaturated hydrocarbon polymers such as polybutadiene, polystyrene, polyisoprene; copolymers of hydrocarbon monomers such as ethylene-propylene copolymers and ethylene-propylene-diene terpolymers (EPDM), polymers of vinyl group monomers containing functional groups such as polyacrylic acid, polymethacylic acid, polyacrylates, polymethacrylates, copolymers thereof such as poly(ethylene-vinyl acetate), carbohydrate polymers such as celluloses, starches, nucleic acids and dextran; polyesters; polyamides; polypeptides; and the like. One of the advantages of the present invention lies in the fact that it can be worked with backbone polymers containing normally unreactive functional groups.

Stable free radical compounds used in the present invention are known and commercially available. There are several different types and classes. One specific preferred class is aminoxyl compounds (also known as nitroxyl compounds or nitroxides), containing an N—O group.

Specific examples include 2,2,5,5-tetramethyl-piperidine-1-oxide (TEMPO)

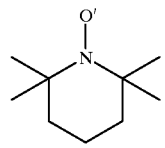

and its amino derivatives such as 4-amino-TEMPO; 3-aminomethyl-PROXYL (AMP):

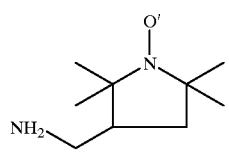

and DOXYL:

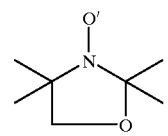

all of which are commercially available.

Another class of stable free radical compounds is aromatic hydrazyl compounds, as represented by 2,2-diphenyl-1-picylhydrazyl:

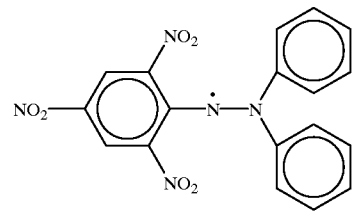

Any stable free radical compound yielding free radicals of lifetime 1 second or greater are useful in the present invention.

The ability to simply and efficiently label polymers, especially those that are difficult to label by other methods, means that the labelling technique of the present invention has many utilities. Binding fluorophores to polymers makes them easy to detect in small concentrations. This is useful for tracking the fate of polymers in the environment. Commercial polymer MW standards labelled in this way can be detected in much lower concentrations. The dynamics of polymer motions and chain-chain interactions are often investigated by fluorescence techniques in both solution and solid states. This labelling technique may be used to rapidly prepare samples for these studies from existing polymers.

The binding of fluorophores (or other labels) to biopolymers is a common procedure. A new labelling technique, particularly one that can be used with difficult to label substrates (e.g. DNA), makes a useful addition to the tools of the biochemist. For example, the ability to label existing DNA strands with a label of the researcher's choice is very useful.

The labelling technique of the invention can be applied to solid polymers to produce solid materials which retain the bulk properties of the polymer but have modified properties at or near the surface. Membranes, biocompatible materials or materials for diagnostics can be prepared in this manner. Photochemical labelling is useful in the printing industry and in the manufacture of printed circuits.

The labelling technique of the invention can be used to introduce a wide variety of labels (chromophores, fluorophores, stable or radioactive isotopes, catalytic groups, biologically active compounds, etc.) onto polymer samples.

The application of the process of the present invention to labelling of nucleic acids (DNA or RNA) provides a particularly advantageous way of determining nucleic acid sequences, by enzymatic sequencing using oligonucleotide primers, nucleic acid units (nucleotides) and polymerase.

Known methods of enzymatic sequencing of nucleic acids use a short oligonucleotide, typically 15–20 nucleotides in length, as a primer. The oligonucleotide primer is complementary in sequence to a portion of the target nucleic acid to be sequenced, so that a duplex is formed between the primer and the target, by hydrogen bonded base pairing. To a mixture of primer and target, in aqueous solution, is added a polymerase and nucleic acids, to cause extension of the primer in a sequence complementary to that of the target. Also included in this solution are some 2',3'-dideoxynucleic acids, which will add to the growing nucleic acid chain but will terminate the synthesis, because they carry an H-group on the 3' carbon instead of the —OH group required for addition of further nucleic acid units. Thus, a dideoxynucleic acid forms the 3' terminal group of each nucleic acid chain complementary to the target nucleic acid, and a "nested set" of such chain extension products, of various molecular weights, is obtained.

A label (fluorescence, radioactivity etc.) is attached to the dideoxyanalogs, or to the primer, or to a single nucleotide, so that each resultant nucleic acid chain bears a labelled molecular unit.

Four separate such primer reactions can be run, each reaction using one of the termination dideoxynucleic acid analogs, i.e. dideoxyadenosine triphosphate (dd ATP), dideoxycytosine triphosphate (dd CTP), dideoxyguanosine triphosphate (dd GTP) and dideoxythymidine triphosphate (ddTTP), with each reaction causing the incorporation of the same detectable label. In an alternative method, each dideoxyanalog is differently and distinctively labelled. Then a single experiment can be run.

Since the reaction solution also contains ATP, CTP, GTP and TTP, the chain extension reaction does not terminate at the first complementary base of the target, but only when a dideoxyanalog reacts, which is a random event. Consequently, the chain lengths of the resulting nucleic acids are dependent to some extent on the relative amount of dideoxyanalog included in the initial mixture.

The resulting products are separated by gel electrophoresis, according to their molecular weight. The identity of the 3' end group of each product is known, from the identity of the dideoxy analog which caused the termination. This is determined either from the identity of the separate primary reaction which was run, or from the distinctive signal of the individual dideoxy analog when a single primary reaction is run containing all four, distinctively labelled dideoxy analog. From a knowledge of this identity, and the molecular weight of the product, the identity of the complementary nucleic acid at the corresponding position of the target sequences is determined. A sufficient number of size variety of such products allows a full determination of the target sequence.

A significant drawback to the above method is that it is in practice limited to sequence determinations of nucleic acids only up to about 500 base pairs in length. Since each macromolecule resulting from the nucleic acid chain extension carries only a single labelled group, the intensity of the signals from the label becomes too low for effective resolution, as the molecular size increases beyond about 500 base pairs.

In alternative prior art process, such as end labelling of the primer with radioactivity, fluorescence or the like, the same problem arises. Only a single labelled unit can be incorporated in each product of the "nested set", so that the intensity of the emission from the labelling becomes relatively smaller as the chain length of the product increases, until it is too indistinct for practical purposes beyond the chain length of about 500 base pairs.

The application of the process of the present invention to nucleic acid sequencing also involves an enzymatic chain extension to form a "nested set" of chain extension products, complementary to the target nucleic acid sequence, and each terminating in a dideoxy nucleic acid analog of known identity, as in the case of the previously described process. Separation of the products according to molecular weight is also conducted. However, in the process of the invention, the label (radioactivity, fluorescence etc.) is applied to the products after the chain extension reaction has been terminated. Labelling is conducted in a random manner, by chemical reaction of the chain extension products, with appropriate labelling compounds.

Accordingly, the process of the invention allows the attachment of a plurality of labelling groups to each product of the "nested set", as opposed to the process described above, which is limited to a single labelling group on each product, whether it is the terminator or the primer which is labelled. Products resulting from the process of the invention can thus provide a significantly higher intensity of signals provided by the labelling groups, for the same molecular weight of product, allowing resolution of higher molecular weight products and in consequence the sequencing of target nucleic acids of greater numbers of base pairs.

The chemical modification is not limited to chemical modification of the terminal, dideoxy group in the process of the present invention as applied to nucleic acids. This terminal group may or may not be modified, on a random, statistical basis. Any of the nucleic acid units making up the polymer product may be modified. The modification may take place on the phosphate portion of the unit, the ribose or the base portion of the unit. Two or more modifications may occur to the same unit, attaching two labels thereto. It does not affect the operation of the present invention. The detectable signal from each labelled product has an intensity which is dependent upon the number of signal emitting label units which have been attached to the product, which is in turn a function of the amount of label-conferring reactant which has been reacted with the product.

The greater intensity of signal emissions obtainable from the products of the present invention, as compared with the prior art products discussed above, allows the sequencing of larger nucleic acids than previously. The background "noise" against which the signal is determined does not become high enough to obscure the signal, and prevent effective detection and determination of the molecular weight of the source product, until nucleic acids having substantially in excess of 500 base pairs are encountered.

The process of the present invention produces products which all have substantially the same concentration of signal producing label per given number of bases making up the nucleic acid chain. There may, for example, be one label for each 10 base units. This results from the random manner in which the label groups attached to the products, and is a factor of the concentration of reagent used in producing the product. This aids in the determination of the molecular weight of the product, since the signal intensity of products resulting from a single labelling process is proportional to the molecular weight of the products.

The preferred type of label for generating a detectable signal from nucleic acid products of the present invention is a fluorescent chemical group, subsequently detectable by its fluorescent light emissions upon radiation. A variety of fluorescent dye group-containing compounds are available, for chemical bonding to the nucleic acid product without interfering with the fluorescent properties of the resulting product.

Since enzymatic nucleic acid synthesis reactions to produce products according to the present invention are conducted in aqueous solution, it is preferred to use water soluble dyes for chemical bonding to the nucleic acid products. The reaction between the nucleic acid and the fluorescence dye is not necessarily conducted in an aqueous solution, although this is preferred.

In the process of the invention as applied to nucleic acid sequencing, nucleic acid polymer free radicals are created, by hydrogen abstraction. Some of these carbon-centered polymer free radicals react with the dye compound present in the solution, and result in fluorescent groups attached to the nucleic acid polymer. Care must be taken in the selection of solvent in which the reaction takes place, both in this nucleic acid embodiment and when using other polymer starting materials. Solvents which will themselves yield free radicals, e.g. by hydrogen abstraction as the solution is treated, need to be avoided. Thus, toluene and alcohols are not suitable as solvents. Water and benzene are examples of suitable solvents, with water being preferred for reasons given above.

According to another preferred method of the invention as applied to nucleic acid labelling and sequencing, the fluorescent dye group containing molecule present in the reaction solution contains photosensitive groups. Upon irradiation of the reaction solution with light of an appropriately chosen wavelength, free radicals containing the fluorescent dye groups are generated, as well as free radicals from the nucleic acid, for bonding together. An example is dye group-containing molecules having ketone groups, e.g. in a position separating two dye groups. Ketone groups of formula —$CH_2$—CO—$CH_2$— are known to be photosensitive to create free radicals, so that a general reaction represented

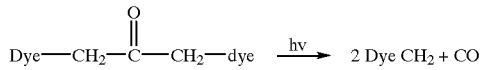

can be adopted. The dye-free radicals need to be sufficiently stable that a concentration of them can be built up in a solution, for reaction with the nucleic acid polymer or radicals thereof, without immediate quenching of the dye-free radicals by recombination or otherwise.

The most preferred process of the invention as applied to nucleic acid sequencing is to include in the reaction solution chemical compounds which are stable free radicals, as in the case of other polymer labelling processes according to the invention. These stable free radicals will react with and bond to free radical sites on the polymers of nucleic acid, and the dye groups can be chemically bonded to the stable free radicals. Alternatively, the dye groups can be chemically bonded to the residues of these compounds after bonding to the polymer through the free radical mechanism. Separation of the polymeric products from non-polymeric products is then conducted, so that fluorescence from the non-polymer bonded dye compound does not interfere with the later detection of signals from the polymeric products. This process allows the use of large quantities of radical-generating chemical compounds in the reaction solution, for greater loading of the nucleic acid polymer products with fluorescence groups.

Examples of commercially available chemical compounds which are stable free radicals and are particularly useful in this work are (2,2,5,5-tetramethylpiperidine)-1-oxide, TEMPO, of chemical formula:

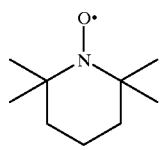

and derivatives thereof.

A solution of nucleic acid polymer and TEMPO derivative can be treated so as to generate free radicals, e.g. by γ-irradiation, light exposure or chemically. The TEMPO compound attaches to radical sites created on the nucleic acid polymer in solution, and then the fluorescent dye is chemically bound to the radical of the TEMPO compound. Also in some cases dye-containing stable free radicals can be reacted with radical sites generated on nucleic acid polymer to produce a fluorophore-labelled product in a single step. Large molar excesses of TEMPO derivative are present in the reaction mixtures, to trap as many potential labelling sites as possible, and to minimize undesirable side reactions of the polymer-centered radicals.

Especially preferred is the use of an amino-derivatized TEMPO spin trap molecule, as the stable free radical generating compound, such as 4-amino-2,2,5,5-tetramethylpiperidine-1-oxide (amino TEMPO). The amino groups attached to the TEMPO residue bonded to the polymer by the free radical mechanism described above are readily reactable with a substantial number of fluorescent dyes available on the market. Such a process preferably uses hydrogen peroxide to generate the free radicals, so that the initial reaction solution comprises the mixture of nucleic acid polymer products, amino-derivatized TEMPO and hydrogen peroxide. The hydrogen peroxide decomposes at room temperature and generates free radicals, as a result of which the amino-TEMPO couples to the nucleic acid products in a random manner and then an appropriate dye such as fluorescein isothiocyanate is added to the reaction mixture and chemically coupled to the polymer through the amino groups of the TEMPO residues attached to the polymer.

In the alternative, the fluorescent dye can initially be coupled to the TEMPO molecule. Such coupled products are available commercially. The coupled product is added to the aqueous solution of nucleic acid polymer products, and the solution subjected to generation of free radicals, e.g. by hydrogen peroxide decomposition. This causes the TEMPO-dye complex to be coupled to the nucleic acid, to form a fluorescent labelled nucleic acid product.

Whilst hydrogen peroxide decomposition is the preferred way of generating the free radicals to effect the coupling of TEMPO and derivatized TEMPO to nucleic acid products, there are alternatives to this. Any system which is capable of generating free radicals in the presence of TEMPO or derivatized TEMPO is suitable, for example, photochemical systems using ketones or anthraquinones, gamma rays emitted from cobalt 60, and the like.

It will be appreciated that the use of fluorescent dye groups as labelling groups or signal units on nucleic acids in the present invention, whilst the preferred embodiment of this aspect of the invention, is not the only way in which the invention can be put into practice. Once the nucleic acid has been derivatized with a molecule such as amino-TEMPO, a variety of different types of labels such as radioactive labels can then be chemically attached to the derivatized nucleic acid. The ability to load the nucleic acid products with relatively large amounts of labelling groups, in a random manner, constitutes the broad concept and practice of this aspect of the invention, encompassing a variety of chemical ways in which this can be accomplished.

Outside of the field of the nucleic acid labelling for sequencing purposes, the present invention provides processes for labelling a wide variety of synthetic and natural polymers to modify their properties in many different ways and for many different purposes. It is applicable in particular to polymers lacking reactive functional groups, and hence lacking reactive sites for chemically labelling by other chemical processes. A wide variety of novel, labelled polymers can be made according to the invention.

The first-step of the process of the invention is one of free radical generation on the polymer, to create free radical sites thereon. This is basically a process of hydrogen abstraction, accomplished by free radical mechanism, and is a random process. There are several ways in which polymer-centered radicals can be generated. These include radiochemical methods, on which the polymer is subjected to irradiation (e.g. with γ-rays from a cobalt-60 source) to create radical species; photochemical methods, in which photosensitive compounds (benzophenone, anthraquinone, polymerization photoinitiators and the like) are included with the polymer and irradiated to produce radicals or excited species capable of creating radical sites on the polymer chain; and chemical methods in which systems such as Fenton's reagent ($Fe^{2+}$/$H_2O_2$) and polymerization initiators (benzoyl peroxide, AIBN, persulfate, etc) produce radical species capable of creating polymer centered radicals. These methods and the various specific embodiments of them are all well-known in the art. The preferred choice is normally based upon the chosen polymer system.

This radical generation process is conducted on the polymer in solution, suspension or dispersion in the presence of the stable free radical generating compound, normally an aminooxyl compound, as described above. The stable free radical compound may have a labelling group or compound attached to it at the time of radical creation on the polymer to cause chemical attachment of the stable free radical to the carbon-centered free radical so formed. Alternatively, the stable free radical may first be chemically bonded to the polymer, and then the labelling group or compound is attached to it.

The ability to simply and efficiently label polymers, especially those that are difficult to label by other methods, means that the labelling technique disclosed herein has many applications. Binding fluorophores to polymers makes them easy to detect in small concentrations. This is useful for tracking the fate of polymers in the environment. Commercial polymer MW standards labelled in this way can be detected in much lower concentrations. The dynamics of polymer motions and chain-chain interactions are often investigated by fluorescence techniques in both solution and solid states. This labelling technique may be used to rapidly prepare samples for these studies from existing polymers.

The binding of fluorophores (or other labels) to biopolymers is a common procedure. A new labelling technique, particularly one that can be used with difficult to label substrates (e.g. DNA), makes a useful addition to the tools of the biochemist. For example, the ability to label existing DNA strands with a label of the researcher's choice may prove very useful.

The invention is further described with reference to the following specific examples.

For the experimental work reported below, amino-TEMPO (AT), 3-aminomethyl-PROXYL (AMP), sodium metabisulfite, anthraquinone (AQ) 2-anthaquinonesulfonate, sodium salt (AQS), 2,6-anthaquinonedisulfonate, disodium salt (AQDS), polystyrene (280,000 g/mol), poly(acrylic acid) (90,000 g/mol), fluorescamine and fluorescein isothiocyanate (FITC) were purchased from Aldrich Chemical Co. and used as received. Ammonium persulfate (BDH), hydrogen peroxide (ACP Chemicals), dextran (Polysciences), poly(ethylene oxide) (Polysciences, Pressure Chemical), poly(sodium 4-styrenesulfonate) (Pressure Chemical), polyvinylpyrrolidone (BDH), BODIPY-FL, SE (4,4-difluoro-5, 7-dimethyl-4-bora-3a,4a-diaza-s-indacene-3-propionic acid, succinimidyl ester) and BODIPY-FL, SSE (sulfosuccinimidyl ester, sodium salt) (both Molecular Probes), DNA (single-stranded (Sigma), 50 base-pair molecular weight ladder (Pharmacia Biotech)) were used as received. Poly(N-isopropylacrylamide) (P(NIPAM)) and 2-anthraquinonylmethyl triethylammonium bromide had been prepared in this laboratory previously. Deionized water from a Milli-Q water purification system (Millipore) was used to make all aqueous solutions. Methanol (Caledon, spectrograde), tetrahydrofuran (THF, ACP Chemicals, reagent grade) were used as received.

EXAMPLE 1

Chemical Labelling of Single-Stranded DNA

Single-stranded DNA (Sigma, denatured, 1.02% aqueous solution, co-migrates with 587–831 base pair marker fragments) was used in this experiment. Three samples were prepared with each containing 20 µL of the 1.02% DNA solution and 400 µL of an aqueous 39.6 mM amino-TEMPO solution. The solutions were bubbled with nitrogen for 10 minutes and then 80 µL of hydrogen peroxide (0.75%, 3%, or 6%) was added with vigorous stirring. The three samples had final concentrations of [DNA]=0.04%; [amino-TEMPO]=31.7 mM; [$H_2O_2$]=35, 141, or 282 mM. The samples were maintained at room temperature (ca. 22° C.) for 80 minutes.

The samples were purified by ultrafiltration in a microcentrifuge. The samples were transferred to centrifuge tubes equipped with ultrafiltration inserts (Gelman NanoSpin Plus, 30000 Molecular Weight Cut-Off). The sample was spun in a microcentrifuge at 10,000 rpm (ca. 6000×g) until the sample volume was reduced to ca. 20 µL. The retentate which includes the DNA) was washed twice by adding water (ca. 400 µL) and spinning in the microcentrifuge until the retentate volume was ca. 20 µL. To the retentate in the ultrafiltration insert was added 100 µL of water, 75 µL of pH 10 buffer, and 60 µL of 11.6 mM fluorescamine (Aldrich) in acetonitrile. After 10 minutes the solution volume was reduced to ca. 20 µL by spinning in the microcentrifuge. The retentate was washed 2 times with water. The final retentate was diluted with water to give a total volume of 400 µL.

Gel permeation chromatography (GPC) was used to analyse the samples. The equipment used to perform GPC consisted of a Waters U6K injector, a Waters 6000A solvent delivery system, a Waters R401 differential refractometer, and an Applied Biosystems 980 fluorescence detector. The samples were passed through a Shodex KB-806M size exclusion column (molecular weight range: 500–$10^7$ g/mol) with water (1.0 mL/min) as the mobile phase The fluorescamine/amine adduct was excited at 385 nm and a 470 nm long pass filter was used to ensure that only emission from the fluorescamine/amine fluorophore reacted the detector.

The GPC chromatograms for the three samples are shown in FIG. 1, with response in arbitrary units plotted as ordinate against retention time (minutes) as abscissa. A chromatogram of a DNA sample treated identically, except that no hydrogen peroxide was added, was prepared for comparison purposes. All chromatograms contain refractive index (RI) peaks of similar intensity at 5.2 min which is due to the DNA. Coincident with these RI peaks in the three treated samples are fluorescence peaks which grow in intensity as the amount of hydrogen peroxide used during labelling increases. This demonstrates that efficient labelling has occurred and that the degree of labelling is related to the amount of hydrogen peroxide used in the reaction mixture. It is also important to note that there is no change in the RI peak over the four chromatograms, which shows that the DNA is not cleaved or crosslinked upon exposure to hydrogen peroxide/amino-TEMPO.

It is possible to calculate the number of fluorescamine/amine fluorophores added per DNA chain or per nucleotide from the intensity of the fluorescence, by comparison with a model compound. The adduct formed by reaction of fluorescamine with ethanolamine was added as the model compound. Comparison of FIG. 1 with a chromatogram of the model compound revealed that the DNA labelled in the presence 35, 141, and 282 mM hydrogen peroxide bore one fluorescamine/amine fluorophore for every 136, 77, and 48 nucleotides, respectively. Assuming an average chain length of about 700 nucleotides, this corresponds to 5.1, 9.1, and 14.6 fluoropores per chain, respectively.

EXAMPLE 2

Photochemical Labelling of Single-Stranded DNA

To a quartz cell were introduced 20 $\mu$L of 1.02% single-stranded DNA (as used in Example 1), 0.5 mL of aqueous 36 mM amino-TEMPO, and 0.5 mL of aqueous 10 mM anthraquinone-2,6-disulfonate, disodium salt. The mixture was degassed with nitrogen for 15 minutes and then irradiated in a Rayonet RPR-100 photoreactor equipped with sixteen 300 nm low pressure mercury lamps. These lamps provide a broad band of light from 270 to 350 nm. Samples (300 $\mu$L) were removed after 30, 60 and 100 minutes of irradiation. The three samples were purified, reacted with fluorescamine, and further purified as described in Example 1. At the end of purification each sample was diluted to 500 $\mu$L with water.

Analysis was conducted by GPC as described in Example 1 and the three chromatograms are shown in FIG. 2. FIG. 2A shows the fluorescence curve 22 and the RI curve 24 from the 30 minutes irradiated sample. FIG. 2B shows the fluorescence curve 26 and the RI curve 28 from the 60 minutes irradiated sample. FIG. 2C shows the fluorescence curve 30 and the RI curve 32 from the 100 minutes irradiated sample. Each chromatogram displays a small RI peak and a larger fluorescence peak at 5 min. Also, the longer the sample was irradiated, the greater the intensity of the fluorescence peak. It may be estimated that the DNA which was irradiated for 100 min bears one fluorophore for every 500 nucleotides, or about 1.4 fluorophore per chain on average. Thus, photochemical labelling of DNA with anthraquinonedisulfonate acting as a hydrogen abstractor was successful. Other compounds which generate hydrogen abstractors upon exposure to light such as ketones, quinones, peroxides, etc. are also useful.

Steady state fluorescence spectra were measured with an SLM 4800 spectrofluorometer.

In FIG. 3 are displayed the excitation spectrum A and emission spectrum B of the DNA labelled as described above. The excitation ($\lambda_{em}$=480 nm) and the emission ($\lambda_{ex}$= 385 nm) spectra are typical of the fluorescamine/amine adduct. This confirms that amino-TEMPO groups were bound to the DNA and that the amino groups were reacted with fluorescamine to form a fluorescent label on the DNA chain.

EXAMPLE 3

Radiochemical Labelling of Single-Stranded DNA

A solution containing 0.2% single-stranded DNA and 61.9 mM amino-TEMPO was prepared and then 0.5 mL Was transferred to each of 4 vials. Each sample was degassed by bubbling with nitrogen for 5 minutes and then sealed with a rubber septum. The samples were then exposed to $\gamma$-rays, produced by a $^{60}$Co source such that they received 0, 0.5, 1.0, or 2.0 Mrad doses of $\gamma$-rays. The samples were purified as described in Example 1. To the retentate (ca. 20 $\mu$L) was added 75 $\mu$L of 0.17M sodium bicarbonate, and then 10 $\mu$L of 11.8 mM fluorescein isothiocyanate (Isomer 1, Aldrich) in anhydrous dimethylformamide. The solutions were mixed on a vortex mixer, left to stand for 50 minutes at room temperature, and then purified as described in Example 1.

Analysis was conducted by GPC as described in Example 1. Each chromatogram displays an RI peak at 5.2 min but only samples exposed to $\gamma$-rays display a fluorescence peak. The presence of a fluorescence peak shows that labelling induced by exposure to $\gamma$-rays has occurred.

EXAMPLE 4

DNA (50 base-pair molecular weight ladder, 1 $\mu$g/$\mu$L in TE buffer, Pharmacia Biotech, catalog #27-4005-01) was used in these experiments. The DNA consists of nucleic acid polymer chains of 50, 100, 150, etc. bases in length, with the 250 base chains in roughly double the concentration of chains of any other length. As received this sample contains no fluorescent labels. It was labelled by the following procedure.

The TE buffer was removed from the sample so as not to interfere with labelling. 10 $\mu$L of the DNA solution (10 $\mu$g of DNA) was purified by centrifugal ultrafiltration (30,000 molecular weight cut-off) as outlined in Example 1. A 57.5 $\mu$L solution containing the purified DNA (ca. 10 $\mu$g), hydrogen peroxide (153.5 mM) and AT (40.8 mM) was deaerated, and then left for 90 min at room temperature. The DNA was then purified by centrifugal ultrafiltration. The purified DNA solution (ca. 20 $\mu$L) was then mixed with ca. 100 $\mu$L of 0.185 M NaHCO$_3$ and 10 $\mu$L of 10.2 mM BODIPY-FL (sulfosuccinimidyl ester in DMSO) and left to stand at room temperature for 1 hour. The sample was purified by centrifugal ultrafiltration.

Half of the purified sample (ca. 5 $\mu$g DNA) was analyzed with an ABI 373 automatic sequencer (gel electrophoresis). The raw data (fluorescence intensity vs. run time) from the sequencer is shown in FIG. 4. Note: the four curves in FIG. 4 arises because the fluorescence intensity is measured through four separate filters. In our experiment the four curves simply reveal the amount of BODIPY-FL emission that passes through each filter. Curve (d) gives the highest response.

FIG. 4 displays a set of strong, regularly spaced peaks. One peak is significantly stronger than the others and is due to the chains of 250 bases in length. With this marker it is possible to assign the peaks as being due to chains of 50, 100, 150 . . . 1050 bases in length. Aside from an impurity peak between the 50 and 100 base peaks, the baseline is smooth which demonstrates that labelling has occurred without any degradation of the DNA chains. With the exception of the peak due to the 250 base chains, the peaks are of similar intensity with no loss of intensity at higher chain lengths.

The regularly spaced peaks in FIG. 4 display further fine structure or splitting. Similar, and more clearly displayed, splitting patterns were observed in a number of other experiments. The unusual splitting pattern is repeated in every fifth peak. For example, peaks for chains of 200, 450 and 700 bases in length displayed the same splitting pattern. In addition, the peaks show a small reproducible variation in peak intensity which repeats with every fifth peak. The reproducible, non-Gaussian splitting which repeats its pattern every fifth peak indicates that the splitting is not due to differing degrees of labelling but to some polydispersity in the initial DNA sample (i.e. the sample may contain chains of 199 and 201 basis in addition to the 200 base chain). If the synthesis of the MW ladder involves construction of the 200, 450 and 700 base chains from the same building block(s) this might explain the similar splitting patterns. The ability to reveal the fine splitting within the major bands of the 50 base-pair MW ladder demonstrates the strong potential of this simple labelling technique.

In order to obtain data for chain lengths in excess of 1000 bases, two consecutive sequencer runs were conducted on a gel containing a BODIPY-FL labelled DNA sample. Thus, the other half of the sample prepared above was analyzed during a normal duration sequencer run (ca. 14 h). Several hours after the first run ended, the buffer was changed and a second 14 h run was performed on the same gel which now contained the partially eluted DNA sample. The results are shown in FIG. 5.

Apart from some impurities which are visible near the beginning of the data (ca. 50 bases) and the marker peak at 250 bases, all the peaks up to about 1400 bases have nearly the same area and are easily resolvable, confirming that the number of labels is proportional to the length of each DNA molecule.

Thus, unlike conventional sequencing methods, the fluorescence response is nearly independent of the number of bases in the DNA chain. Furthermore, the peaks are relatively sharp and should be resolvable up to 1400 bases, possibly longer if the electrophoretic conditions were optimized.

EXAMPLE 5

Photochemical Labelling of Poly(Acrylic Acid)

Poly(acrylic acid) (90,000 g/mol); 0.102 g), AQDS (4.3 mg) and AT (10.0 mg) were dissolved in 10 mL of water. The solution was placed in a quartz tube, deoxygenated by bubbling with nitrogen for 10 minutes, and then irradiated with a Rayonet RPR-100 photoreactor (16×300 nm lamps). Samples (3 mL) taken before irradiation and after 40 minutes irradiation were adjusted to pH >7 with NaOH solution or pH 10 buffer before the addition of 0.6 mL of 0.09% (w/v) fluorescamine in acetonitrile. The solutions were transferred to dialysis tubing (Spectra-Por, 12-14000 molecular weight cut-off) and exhaustively dialyzed with water. The purified polymer solutions were then analysed by UV/visible spectroscopy and gel permeation chromatography, generally as described in Example 1.

The photochemical generation of polymer-centered radicals was extended and repeated to label several different polymers (Table 1). Polymer centered radicals were generated by abstraction of H atoms with photochemically excited anthraquinone or peroxy compounds. The anthraquinone chromophore was selected because: 1) it is a good H-abstractor, and 2) the characteristic absorption at ca. 330 nm is not obscured by the absorption of amino-TEMPO (ca. 405 nm). In addition, anthraquinone and peroxy compounds are converted to radicals which bear much of the unpaired electron density on an oxygen atom and, thus, do not react with amino-TEMPO.

Most of the experiments reported in Table 1 involved labelling in aqueous media and anthraquinone-2,6,-disulfonate, disodium salt (AQDS) was used as the H-abstractor in most of the experiments.

Following binding of the AT group to the polymer chain, AQDS and excess AT were removed, fluorescamine was added and then small molecule impurities were removed by dialysis or ultrafiltration. Fluorescamine reacts with primary amines to produce highly fluorescent adducts.

TABLE 1

Results of photochemical labelling experiments.

| POLYMER | LABELLING SYSTEM | RESULT |
| --- | --- | --- |
| PEO, 300k | Hv/AQDS/AT + fluorescamine | labelled + degradation |
| PAA, 90k | hv/AQDS/AT + fluorescamine | labelled |
| Dextran, 75k (MW std) | hv/AQDS/AT + fluorescamine | labelled |
| PSSS, 200k (MW std) | hv/AQDS/AT + fluorescamine | labelled |
| PSSS, 46k (MW std) | hv/AQMTEA/AT + fluorescamine | ca. 4 labels/chain |
| PVP, 44k | hv/AQS/AT + fluorescamine | labelled |
| DNA, ≈200k | hv/AQDS/AT + fluorescamine | labelled, proportional to irradiation time |
| PS, 280k | hv/AQ/AT + BODIPY-FL, SE | labelled, proportional to irradiation time |
| PMMA, 25k | hv/(tBuO)$_2$/AT + BODIPY-FL, SE | labelled |
| PS, 4.75k (MW std) | hv/(tBuO)$_2$/AT + BODIPY-FL, SE | labelled |

Figure 6:
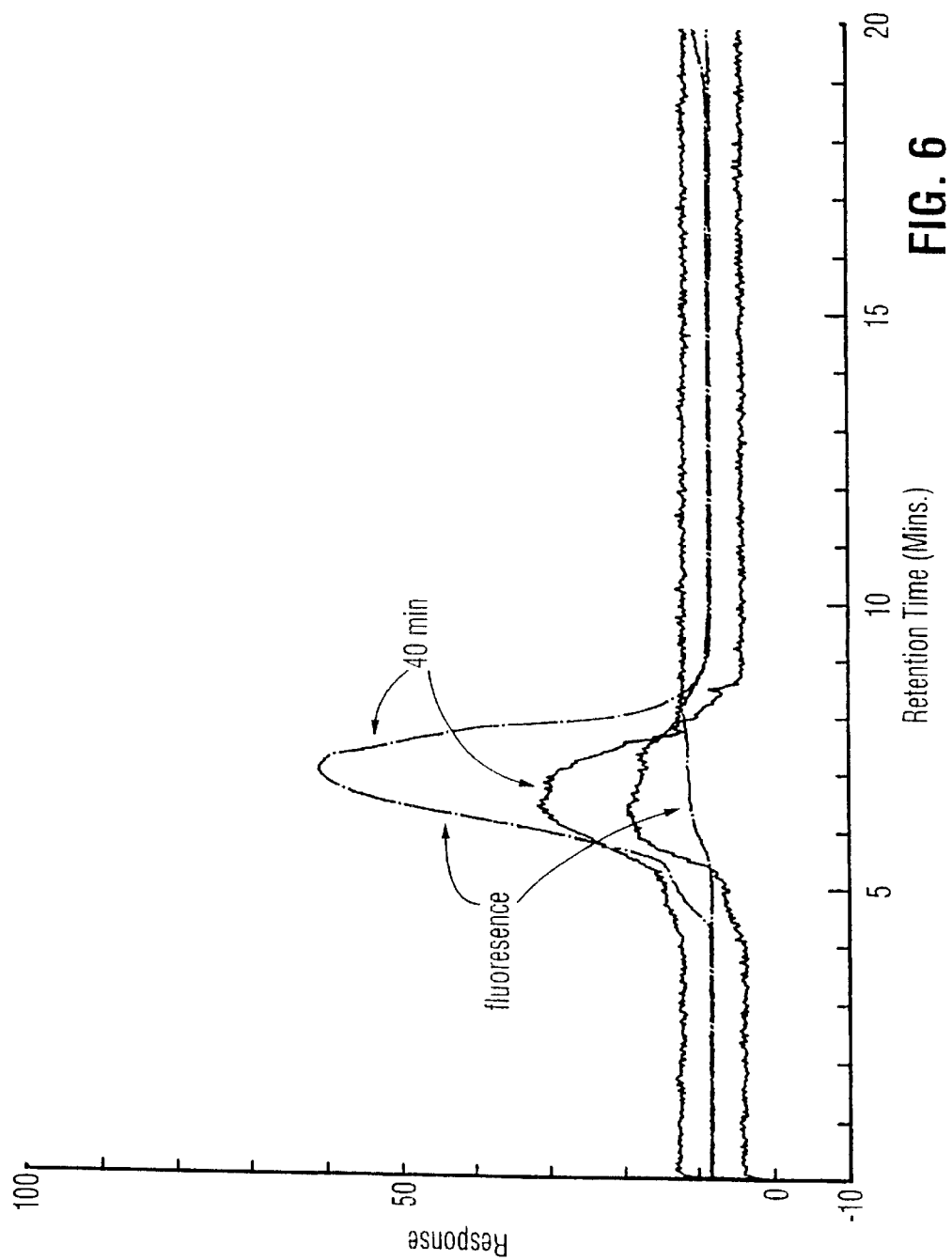
Figure 7:
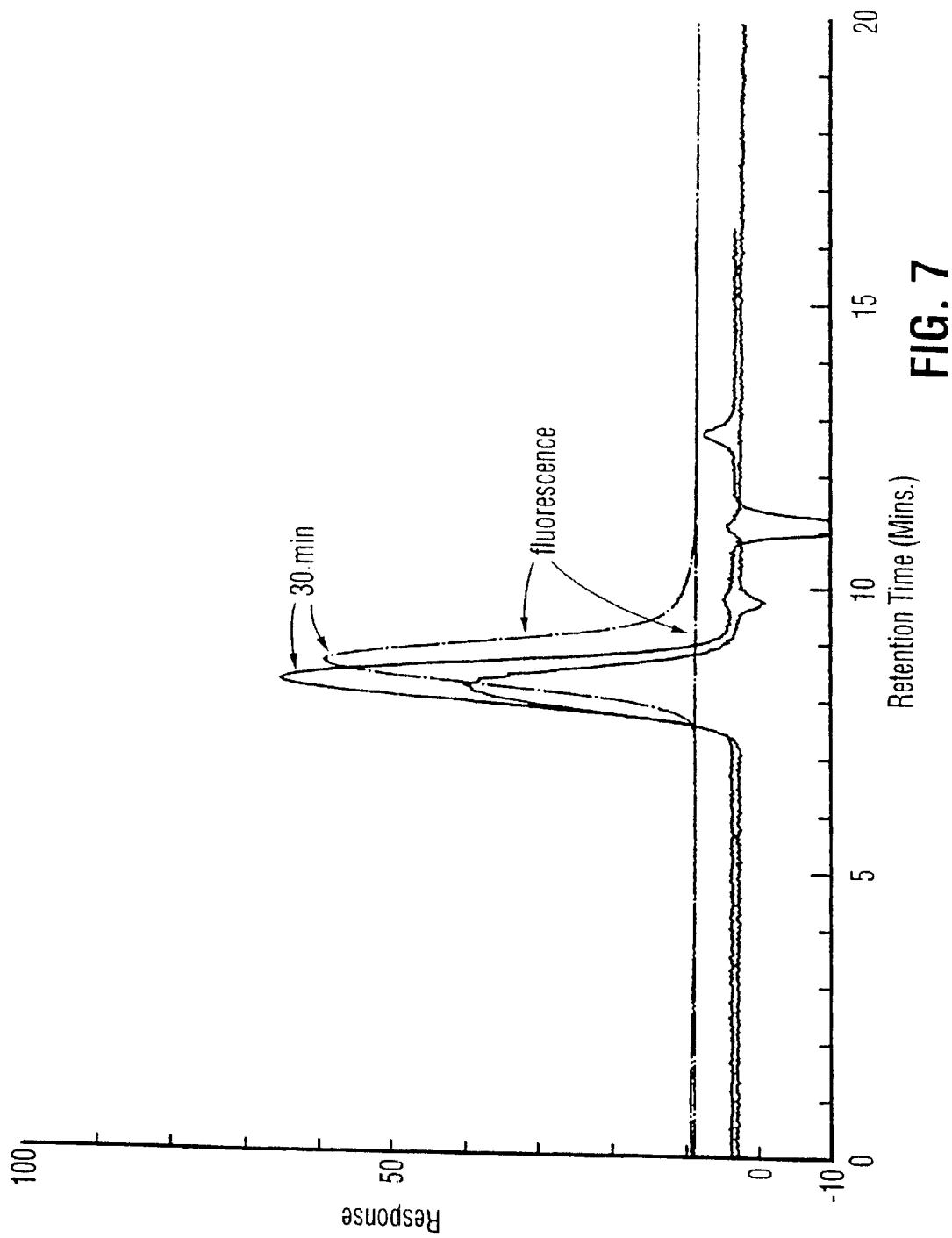
Figure 8:
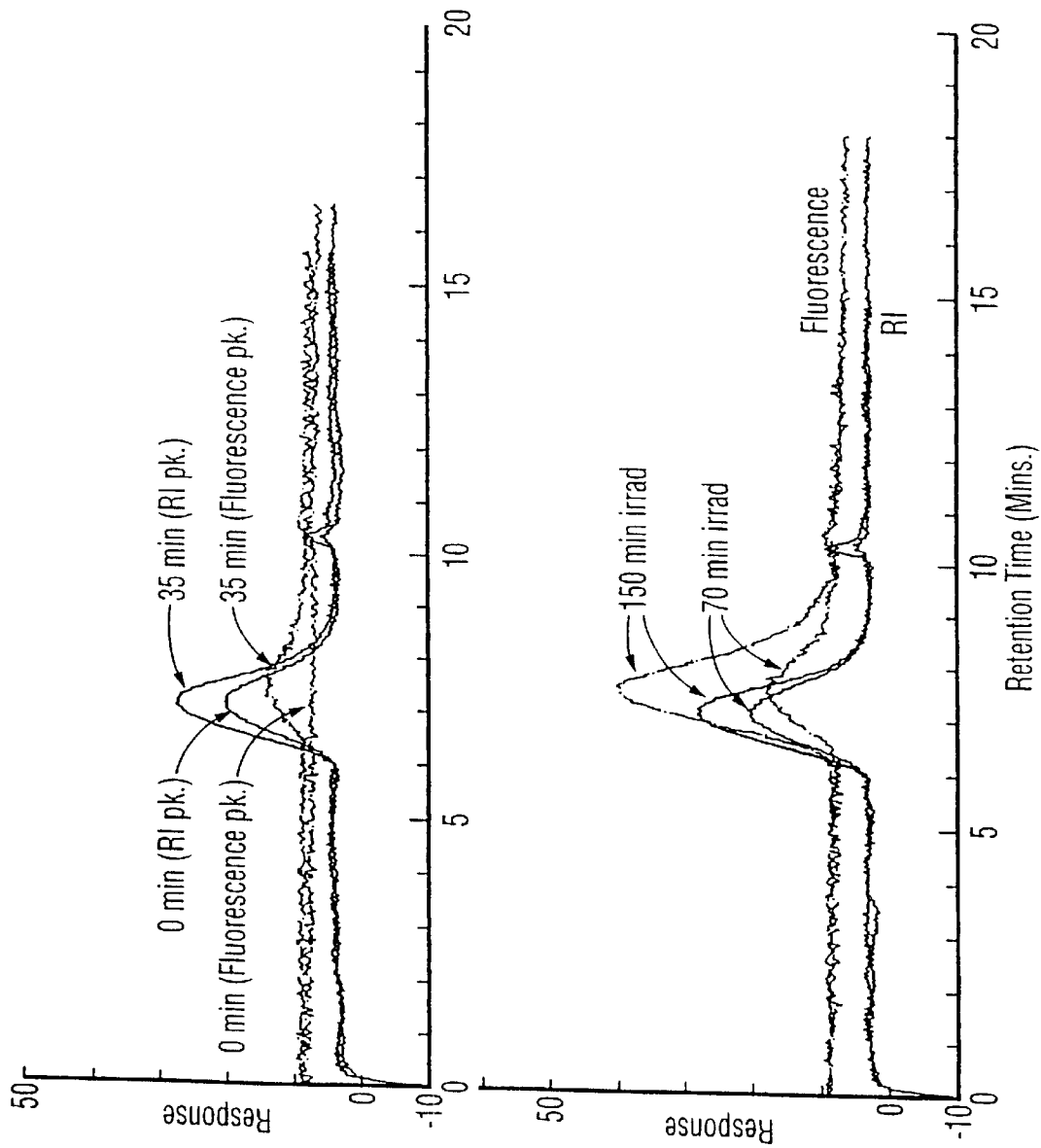
Figure 9:
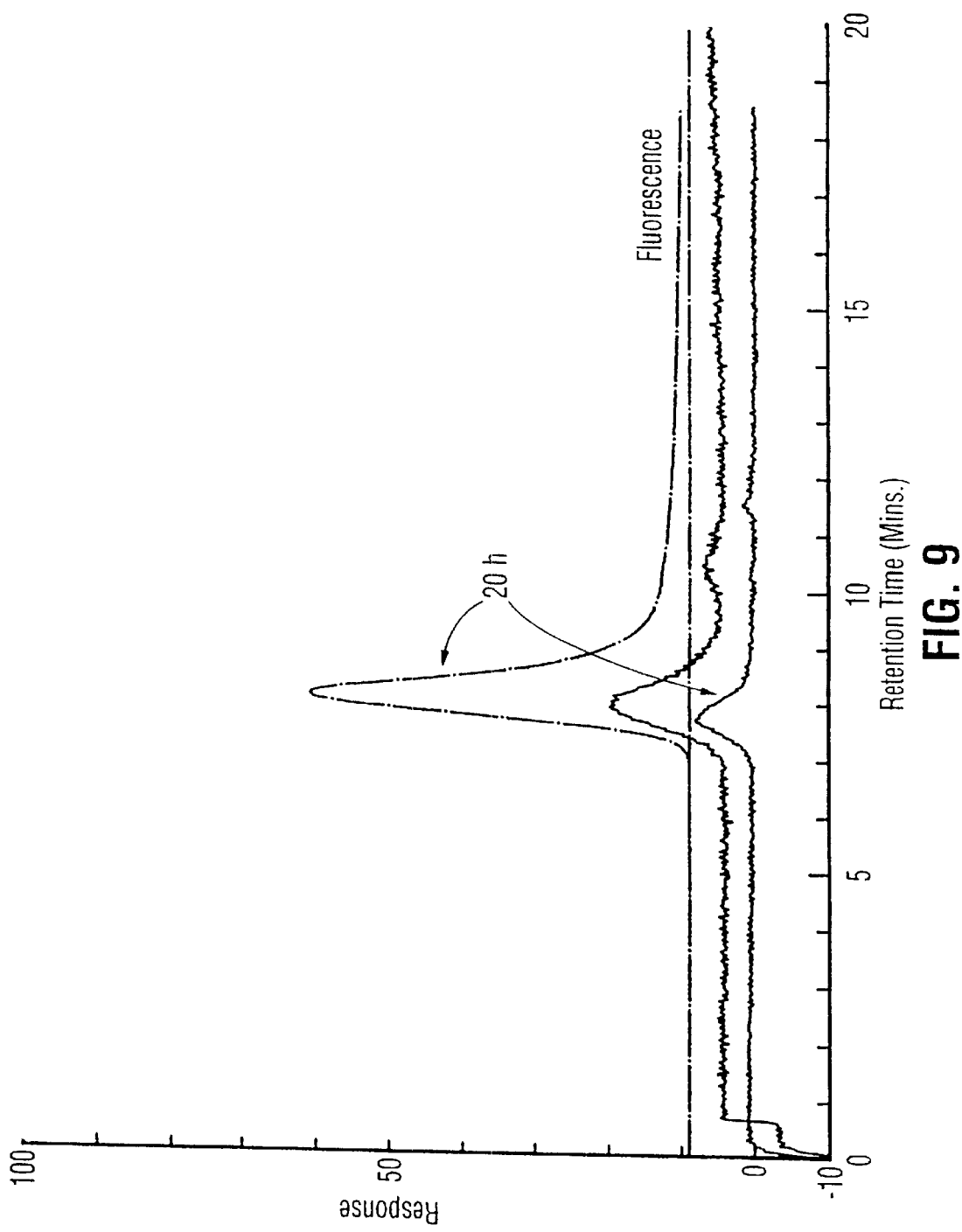
Figure 10:
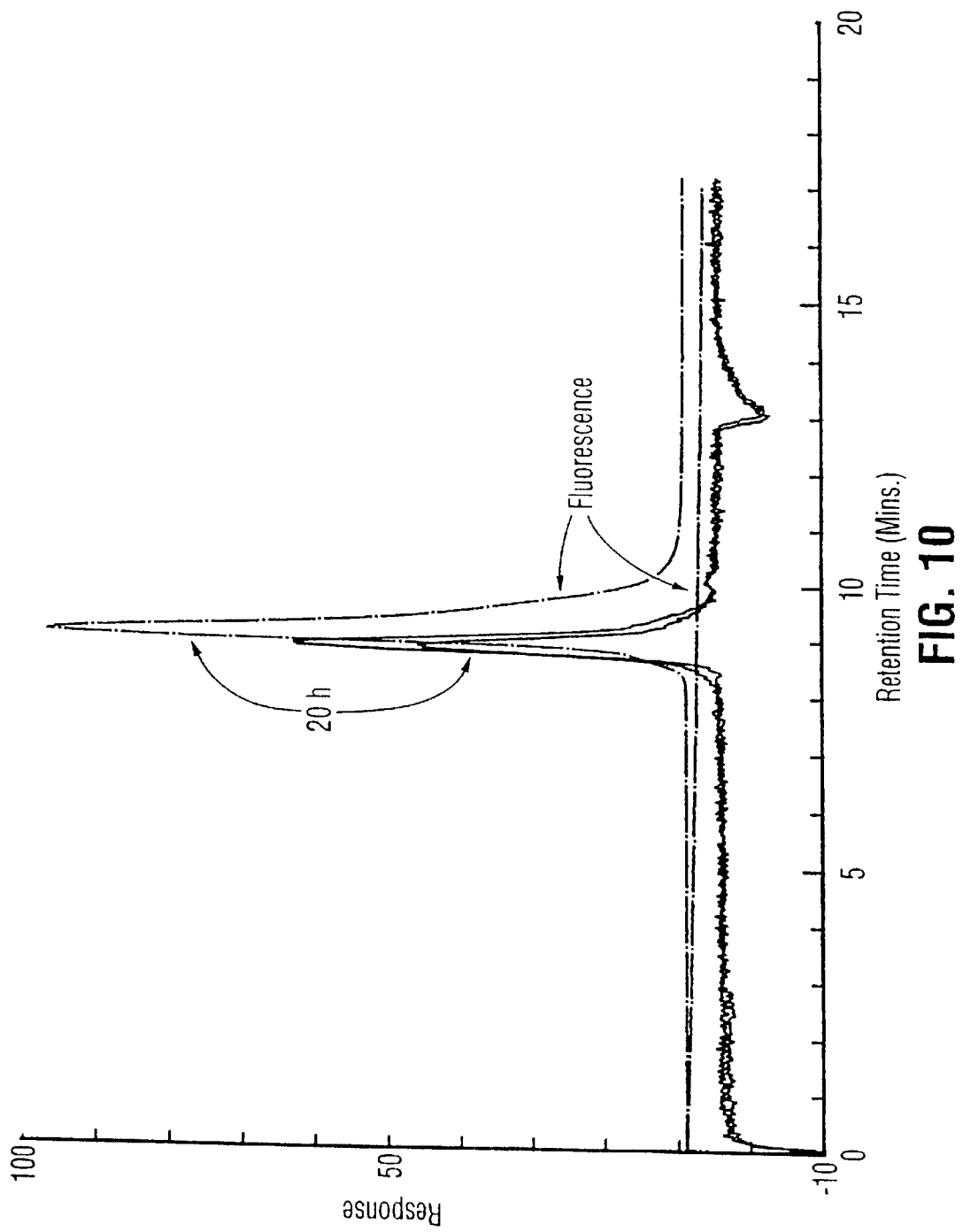

PEO, PAA, dextran, PSSS and DNA were all successfully labelled with the AQDS/light/AT system while PVP was labelled in the presence of the closely related 2-anthaquinonesulfonate (AQS). GPC traces for PAA and dextran are shown in FIGS. 6 and 7. The strong fluorescence peak ($\lambda_{ex}$≈380 nm; $\lambda_{em}$≧470 nm) coincident with the polymer RI peak reveals that the polymers bear the fluorescamine/AT adduct. In the case of PAA, an exhaustively dialyzed sample showed an easily detected absorption at 385 nm in the UV-visible spectrum which confirms that the fluorescamine/AT adduct is bound to the polymer chain.

Photochemical labelling of PSSS was conducted in the presence of AQDS or AQMTEA ((2-anthraquinonylmethyl) triethyl-ammonium bromide), a cationic anthraquinone compound. PSSS was labelled in both experiments but occurred to a lesser extent with AQDS. In the case of AQMTEA, a 25 minute irradiation was found to result in the binding of about 4 AT groups per 46,000 g/mol PSSS chain (assuming 100% reaction between fluorescamine and the bound AT groups). The reduced extent of labelling observed with AQDS is likely due to electrostatic repulsion between PSSS, a polyanion, and AQDS, a dianion, which hinders the H-abstraction reaction.

Samples of polymer/AQDS/AT which were not exposed to light but otherwise treated in the same manner as irradiated samples showed no detectable labelling. As the irradiation time increased, the polymers showed higher degrees of labelling. This means that the creation of polymer-centered radical which allows binding of AT is a photochemical process and AT is not bound as the result of a dark reaction.

The final experiments reported in Table 1 involve photochemical labelling in organic solvent and demonstrate that labelling may be carried out in organic as well as aqueous media. The photochemical labelling of PS with AQ/AT in benzene followed by reaction with BODIPY-FL, SE yielded a labelled polymer with fluorescence that was easily detected by eye. GPC analysis revealed a strong fluorescence peak (FIG. 8) and the strength of the signal was found to be proportional to the irradiation time used during labelling.

Organic soluble samples were analyzed on a Waters GPC (U6K injector, 510 pump) equipped with two 30 cm Zorbax PSM columns (60S and 1000S), a Waters R401 differential refractometer, and an ABI 980 fluorescence detector. The fluorescamine/amine adduct was excited at 385 nm and a 417 or 470 nm long pass filter was used to ensure that only emission from the fluorescamine/amine fluorophore reached the detector. Fluorescein or BODIPY-FL were excited at 500 nm and a 515 nm long pass filter was used to filter the emission.

The photochemical decomposition of t-butyl peroxide is another means of producing polymer-centered radicals. Both PMMA (FIG. 9) and PS (FIG. 10) were efficiently labelled with AT upon irradiation of benzene solutions containing polymer, t-butyl peroxide and AT. In addition, there are no signs that any polymer degradation has occurred during the labelling experiment.

BODIPY-FL, SE (4,4-difluoro-5,7-dimethyl-4-bora-3a, 4a-diaza-s-indacene-3-propionic acid, succinimidyl ester) was used to bind a fluorophore to the PS and PMMA chains. The BODIPY-FL chromophore has absorption and emission properties similar to those of fluorescein. A wide range of amine reactive dyes are known and many are commercially available.

EXAMPLE 6

Radiochemical Labelling of Polystyrene

Polystyrene (280,000 g/mol; 0.169 g) and AT (0.256 g) were dissolved in 25 mL benzene. 5 mL of this solution was transferred to each of four Pyrex tubes. The samples were degassed by three freeze/pump/thaw cycles before the tubes were sealed. The samples were exposed to 0, 0.5, 1 or 2 Mrads of γ-rays from a $^{60}$Co source. The polymers were precipitated in methanol, filtered, washed with methanol and then air dried. Each polymer sample was dissolved in benzene (1 mL) before the addition of 1 drop of pH 10 buffer and 100 μL of 12.8 mM BODIPY-FL, SE in DMSO. The solutions were mixed on a vortex mixer and then stored at room temperature for 1 hour. The polymer was precipitated in methanol (50 mL), filtered, washed with methanol and then purified by a second precipitation from benzene into methanol. The polymer samples were dried in a vacuum oven (45° C./2 hours) and then dissolved in THF prior to analysis by GPC.

γ-rays are a highly energetic form of radiation which can penetrate deep into a sample where they may create a shower of high energy particles (e.g. electrons, photons, radicals, etc.). Some of these initially-formed particles will create other reactive species. When polymers are exposed to γ-rays, polymer-centered radicals are known to result. If AT is present, then one can anticipate that it will react with the polymer-centered radicals.

P(NIPAM), PAA, DNA and PS were successfully labelled following exposure to γ-rays in the presence of AT (Table 2). For example, the GPC trace for PAA (FIG. 11) shows that the polymer bears fluorescein chromophores and that the degree of labelling is proportional to the dose of radiation. Labelling was easily detected following radiation doses of 0.5 Mrad.

Labelling via the radiochemical generation of radicals was conducted in aqueous or organic (benzene) media and a variety of fluorophores were linked to the polymers following the binding of AT, which again demonstrates the versatility of this labelling technique.

Some evidence of polymer degradation was noted with P(NIPAM), PS and DNA. P(NIPAM) solutions that had been irradiated showed signs of crosslinking. Solutions exposed to 2 Mrads were hazy while those exposed to 5 or 10 Mrads also contained precipitated polymer. It is possible to label P(NIPAM) while reducing the amount of crosslinking, by reducing the radiation dose, lowering the polymer concentration and increasing the concentration of spin trap.

TABLE 2

RESULTS OF RADIOCHEMICAL LABELLING EXPERIMENTS

| Polymer, MW | Labelling System | Results |
| --- | --- | --- |
| P(NIPAM) | γ-rays/AMP + fluorescamine | labelled, cross-linked |
| PAA, 90k | γ-rays/AT + fluorescein | labelled, cross-linked |
| DNA, ≈200k | γ-rays/AT + fluorescein | labelled |
| PS, 280k | γ-rays/AT + BODIPY-FL, SE | labelled, minor degradation |

With PS and DNA it appears that some chain cleavage is occurring since lower molecular weight species were evident in the GPC traces. FIG. 12 displays the GPS chromatogram for a PS sample exposed to 2 Mrads and a shoulder is evident on the low molecular weight side of the fluorescence peak. In contrast, PS that was labelled via the photochemical generation of radicals did not exhibit signs of polymer cleavage (see FIG. 8).

EXAMPLE 7

Chemical Labelling

The procedure of Example 1 was essentially repeated, but using other polymers than DNA, and, of course, without the sequencing steps.

It is common to add catalysts/accelerators to hydrogen peroxide of persulfate to improve the yield of radicals. Thus, most of these examples did not employ hydrogen peroxide or persulfate alone but in combination with a catalyst— Fenton's reagent ($Fe^{2+}/H_2O_2$), persulfate/tetramethylethylenediamine ($S_2O_8^{2-}$/TEMED) persulfate/metabisulfite ($S_2O_8^{2-}/S_2O_5^{2-}$).

PSSS was successfully labelled when Fenton's reagent was used.

Labelling occur red when persulfate was used to generate radicals either alone or in combination with a catalyst. Thus, dextran, PSSS, PVP and DNA were effectively labelled with a fluorophore when persulfate was used to generate polymer-centered radicals. A solution of dextran heated with $S_2O_8^{2-}$/AT at 70° C. for 2.5 hours and then reacted with fluoroescamine gave the GPC chromatogram shown in FIG. 13. The fluorescence peak which is coincident with the RI peak at ca. 8.5 minutes shows that labelling was successful.

Poly(2-vinylnaphthalene) was labelled in organic solution in the following matter. Poly(2-vinylnaphthalene) (0.50 g, ca. 100,000 g/mol), at (87.5 mg) and t-butylperoxide (0.45 g) were dissolved in 10 mL of t-butylbenzene. The solution was deaerated and then heated for 2.5 h at 130° C. at which time the orange solution had turned yellow. The polymer was purified by precipitation into methanol, followed by a second precipitation from dichloromethane/toluene into methanol before drying under vacuum. A 27.2 mg portion of the dried polymer w as dissolved in 0.5 mL THF before the addition of 30 µL of Ph 10 buffer and 20 µL of 12.8 mM BODIPY-FL, SE in DMSO. After 45 min at room temperature, the polymer was precipitated in methanol and then purified by a second precipitation from THF into methanol. The labelled poly(2-vinylnaphthalene) was dried under vacuum and then analyzed with the organic GPC (THF eluant).

The GPC trace (FIG. 14) shows that labelling was successful since there is a strong fluorescence peak coincident with the RI peak for the labelled polymer. The RI peak of the labelled polymer is identical to that for the unlabelled polymer which demonstrates that degradation in the form of chain scission or cross-linking did not occur. Analysis of the peak areas indicates that about 55% of the poly(2-vinylnaphthalene) chains has been labelled.

The specific examples presented in this application involve labelling with fluorophores but a variety of different labels can be bound to polymers with this technique. One can prepare polymer-bound radiolabels (medical imaging, radiation treatment), catalytic groups (hetero/homogeneous catalysts), biologically active groups such as enzymes, receptors (biomaterials, medical diagnostics), drugs (drug delivery), chiral groups (chiral stationary phase for chromotography) and others.

The labelling of polynucleotides according to the present invention is useful not only in connection with DNA and RNA sequencing as described, but also in any processes where detection and/or analysis of polynucleotides is required. This includes various analytical and diagnostic processes which involve polynucleotides and oligonucleotides, e.g. in analysis of mixtures of nucleic acids by hybridization to a polynucleotide probe, detection of nucleotides by application of a family of test polynucleotide compounds, and similar procedures. The use of labelled polynucleotides according to the invention allows for enhanced detection and analysis of polynucleotide products, especially when polynucleotides of long chain sequences are involved.

What is claimed is:

1. A process of labelling a polymer with functional groups randomly distributed along the polymer backbone chain, which comprises:
    generating free radicals at random positions along the polymer;
    reacting the polymer centered free radicals so formed with stable free radicals which are species which will not react with themselves at room temperature and which yield free radicals of lifetime one second or greater, so as to attach stable free radical derived groups thereto at random locations along the polymer chain;
    and attaching functional labelling groups to the stable free radical derived groups, before or after the reaction thereof with the free radicals on the polymer chain.

2. The process of claim 1 wherein the polymer-centered free radicals are generated on the polymer in solution, suspension or dispersion in an inert medium.

3. The process of claim 2 wherein the radical generation is accomplished by radiation, by photochemical formation of active species, or by chemical production of free radicals capable of creating radical sites on the polymer chain.

4. The process of claim 2 wherein the stable free radicals are present in the solution, suspension or dispersion at the time of polymer-centered free radical generation.

5. The process of claim 4 wherein the stable free radicals are aminooxyl compounds.

6. The process of claim 5 wherein the polymer is a synthetic saturated hydrocarbon polymer, a synthetic unsaturated hydrocarbon polymer, a synthetic hydrocarbon copolymer, a polymer or copolymer of a vinyl group-containing monomer, a carbohydrate polymer, a polyester, a polyamide or a polypeptide.

7. The process of claim 1 wherein the functional labelling groups are fluorophoric groups.

8. The process of claim 1 wherein the polymer is a nucleic acid, poly(acrylic acid), poly(ethylene oxide), dextran, polystyrene sulfonate, polyvinylpyrrolidone polystyrene, polymethylmethacrylate or poly(N-isopropylacrylamide).

9. The process of claim 1 wherein the stable free radical groups are derived from 2,2,6,6-tetramethylpiperidine-1-oxide of formula:

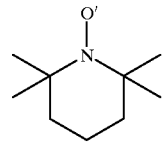

4-amino-2,2,6,6-tetramethylpiperidine-1-oxide, of formula:

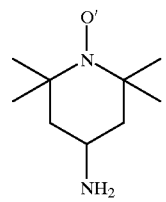

3-aminomethyl-2,2,5,5-tetramethylpyrrolidine-1-oxide, of formula:

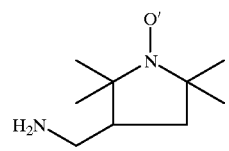

or 2,2,5,5-tetramethyl-oxazole-1-(N)-oxide, of formula:

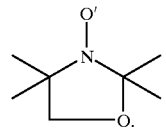

10. A labelled polymer having a polymer backbone chain and a plurality of labelling groups randomly distributed along the polymer backbone chain and chemically bonded thereto by reaction conducted to modify an existing polymer, the labelling groups having a general formula —X—Y wherein the X— group is chemically bonded to the polymer backbone chain as a side group and comprises a group derived from a stable free radical compound, comprising species which will not react with themselves at room temperature and which yield free radicals of lifetime one second or greater, and the Y— group is a functional group bonded to the X— group.

11. The labelled polymer of claim 10 wherein the functional group Y is a fluorophone, a radioactive group, a catalytic group, an enzyme, a biological receptor, a drug or a chiral group.

12. The labelled polymer of claim 10 wherein stable free radical derived group X is an aminooxyl group.

13. The labelled polymer of claim 12 wherein the stable free radical derived group X is derived from 2,2,6,6-tetramethylpiperidine-1-oxide; 4-amino-2,2,6,6-tetramethylpiperidine-1-oxide; 3-aminomethyl-2,2,5,5-tetramethylpyrrqlidine- 1-oxide; or 2,2,5,5-tetramethyloxazole-1-(N)-oxide.

14. The labelled polymer of claim 10 wherein the polymer is a synthetic saturated hydrocarbon polymer, a synthetic unsaturated hydrocarbon polymer, a synthetic hydrocarbon copolymer, a polymer or copolymer of a vinyl group containing monomer, a carbohydrate polymer, a polyester, a polyamide or polypeptide.

15. The labelled polymer of claim 10 wherein the polymer is a nucleic acid, poly(acrylic acid), poly(ethylene oxide), dextran, polystyrene sulfonate, polyvinylpyrrolidone, polystyrene, polymethylmethacrylate or poly(N-isopropylacrylamide).

16. The labelled polymer of claim 10 wherein the reactive functional group Y is a fluorophore.

17. A process of determining the sequence of a target nucleic acid which comprises preparing a mixture of polynucleotides complementary in sequence to portions of the target nucleic acid by PCR chain extension of oligonucleotide primers with random chain growth termination so that the polynucleotides in said mixture have different, random chain lengths; labelling the polynucleotides by the process of claim 1 to bond detectable groups randomly along the length of the polynucleotide chains; separating the mixture of polynucleotides into polynucleotide components of different molecular weight; and determining the presence and end group identity of different molecular weight polynucleotides, by detection of the functional, labelling groups randomly attached thereto.

18. The process of claim 17 wherein the stable free radical groups are derived from 4-amino-2,2,6,6-tetramethylpiperidine-1-oxide.

19. The process of claim 17 wherein the functional, labelling groups are fluorophoric groups.

20. The process of claim 17, wherein some of the polynucleotides of the mixture from which the presence of functional labelling groups are detected are in excess of 300 base pairs in length.

21. A process of labelling polynucleotides, which comprises subjecting the polynucleotides in solution in a non-reactive solvent and in the presence of dissolved stable free radical compound which comprises species which will not react with themselves at room temperature and which yield free radicals of lifetime one second or greater, to hydrogen extraction to create polymer-centered free radicals, whereby said stable free radical compound molecules chemically bond to the polynucleotide in random fashion at the location of the polymer centered free radicals, to provide randomly distributed labels on the polynucleotide.

22. A process of labelling polynucleotides, which comprises mixing the polynucleotides in solution with a fluorescent dye compound containing photosensitive groups, irradiating the mixed solution with light of wavelength which effects generation of stable free radicals containing the fluorescent dye groups and free radicals on the polynucleotides, said free radicals containing the fluorescent dye group being sufficiently stable that a concentration thereof is built up in said solution for reaction with the free radicals on the polynucleotides, and without immediate quenching of said free radicals containing fluorescent dye group by recombination thereof, and allowing the dye group free radicals and the polynucleotide free radicals to bond together to form a polynucleotide randomly labelled with fluorescent dye groups.

23. A labelled polynucleotide comprising a single stranded or double stranded DNA or RNA sequence of at least 500 base units, and having fluorophoric labelling groups attached thereto at random positions along the length of the polynucleotide chain, through the intermediary of a group derived from a stable free radical compound comprising species which will not react with themselves at room temperature and which yield free radicals of lifetime one second or greater, said stable free radical-derived group being chemically bonded to the polynucleotide by reaction conducted to modify an existing polynucleotide.

24. The process of claim 22 wherein said fluorescent dye containing compound contains photosensitive ketone groups of formula —$CH_2$—CO—$CH_2$— separating two dye groups, which produce said stable free radicals upon irradiation with light of appropriate wavelength.

25. The process of claim 22 wherein said stable free radicals containing the fluorescent dye group have a lifetime of one second or greater.

* * * * *